United States Patent [19]
Torre

[11] Patent Number: 4,985,035
[45] Date of Patent: Jan. 15, 1991

[54] REMOVABLE HANDLE FOR BLADED SURGICAL INSTRUMENTS

[76] Inventor: Randall J. Torre, 842 S. Clover, San Jose, Calif. 95128

[21] Appl. No.: 328,441

[22] Filed: Mar. 24, 1989

[51] Int. Cl.$^5$ ............................................. A61B 17/32
[52] U.S. Cl. .................................... 606/167; 606/84; 30/339
[58] Field of Search ...................... 128/305, 305.5, 304; 30/329, 337, 339; 606/82, 84, 85, 160, 167, 170, 176, 79, 110

[56]     References Cited
    U.S. PATENT DOCUMENTS

| | | | |
|---|---|---|---|
| 667,726 | 2/1901 | McDade | 606/160 |
| 1,390,720 | 9/1921 | Powers | 606/167 |
| 1,448,305 | 3/1923 | Langbein | 30/339 |
| 2,257,141 | 9/1941 | Waugh | 30/339 |
| 2,951,482 | 9/1960 | Sullivan | 606/176 |
| 3,262,205 | 7/1966 | Arden | 30/339 X |
| 4,491,132 | 1/1985 | Aikins | 606/170 |
| 4,586,496 | 5/1986 | Keller | 606/84 |
| 4,633,866 | 1/1987 | Korth et al. | 606/170 |

FOREIGN PATENT DOCUMENTS 397655  8/1933  United Kingdom .................. 30/339

OTHER PUBLICATIONS

American V. Mueller, "The Surgical Armamentarium", (1980), p. 508.
American V. Mueller, "The Surgical Armamentarium", (1980), p. 3.

Primary Examiner—Michael H. Thaler
Attorney, Agent, or Firm—Schroeder, Davis & Orliss Inc.

[57]     ABSTRACT

A surgical instrument provides a handle for removably attaching blades having different sizes and different purposes for performing different surgical procedures.

14 Claims, 8 Drawing Sheets

REMOVABLE HANDLE FOR BLADED SURGICAL INSTRUMENTS

BACKGROUND OF THE INVENTION

The present invention relates generally to surgical instruments and, more particularly, to a removable handle to which a number of different sized and different purpose bladed surgical instruments may be removably attached.

Typically, a physician will utilize a large number of single-bladed surgical instruments such as surgical osteotome or capsular releasing instruments. The surgical osteotome, for example, is a surgical instrument specifically designed for assisting a surgeon in the removal of fibular material at a joint such as a nodular mass of bone or cartilage in a tendon known as a sesamoid, associated with bunion procedures, and other sesamoidal related procedures such as removal of non-union tribial sesamoids or painful supernumerary bones. The surgical osteotome consists of three parts, a handle, an extension or shaft and a blade. Similarly, capsular releasing instruments consist of a handle, a shaft and a blade. The primary difference between the instruments being shape and configuration of the shaft and blade to adapt to different uses.

It is well-known in the prior art to provide bladed surgical instruments of the type described above. Typically, the prior art bladed instruments are fabricated as an integral unit thus requiring the physician or medical facility to obtain a large number of separate instruments, often at great expense. Further, the handle portion of the bladed instrument is typically the largest and heaviest portion of the bladed instrument requiring bulky storage and transport cases.

SUMMARY OF THE INVENTION

In accordance with the principles of the present invention, a number of bladed surgical instruments comprising a removable handle interchangeable with a number of different sized and shaped blade extensions and blade sections are provided. In a first embodiment a surgical releasing myo-osteotome instrument comprises three interchangeable units, a handle, an extension and a blade. The handle has an internally threaded bore extending lengthwise into the distal end. Each of several different extension sections are externally threaded at the proximal end to facilitate insertion into and removable attachment at the distal end of the handle. Blades for the instrument are provided as sterile, pre-packaged units and removably snap-on to the distal end of the extension section.

In a second embodiment a capsular releasing instrument comprises a removable handle interchangeable with a number of different blade sections. Each blade section comprises an integral shaft having a blade of the desired shape and size formed at the distal end thereof. The handle is constructed as described hereinabove having an internally threaded bore extending lengthwise into the distal end of the handle. Similarly, the blade shaft is externally threaded at the proximal end thereof to facilitate insertion into and removable attachment to the handle.

The handle is fabricated with an indented area on the dorsal distal aspect of the handle contoured to accommodate a human thumb allowing a user to maintain control and stability of the instrument during a surgical procedure. The extensions and shaft sections are fabricated in various sizes and curvatures to adapt to the various curvatures of the bones and bone joints encountered in the human body. Similarly, the blades are fabricated in various sizes and configurations. The several interchangeable extensions, shafts and blades provide a wide selection of surgical instruments when utilized with one or more interchangeable and removable handles. The expense to acquire a complete set of surgical osteotome instruments, for example, is substantially reduced as is the size and weight of storage and transportation cases.

DETAILED DESCRIPTION OF THE PREFERRED EMBODIMENTS

Figure 1:
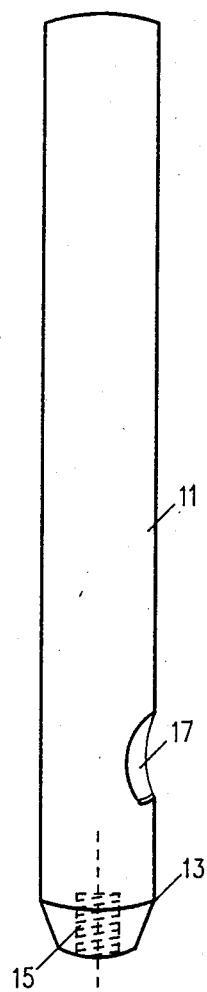
FIG. 1 is a perspective view showing a first embodiment of a removable handle constructed according to the principles of the present invention.
Figure 2:
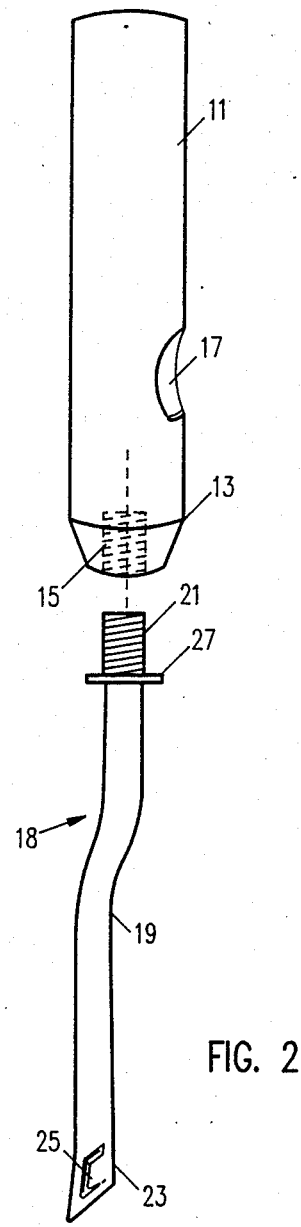
FIG. 2 is a perspective view illustrating the removable handle shown in FIG. 1 with an interchangeable extension section constructed according to the principles of the present invention.

Referring now to FIGS. 1 and 2, an interchangeable, removable handle 11 and extension section 18 constructed according to the principles of the present invention are shown. The handle section or handle 11 is generally round and preferably straight and may be slightly bevelled at the distal end 13 thereof. To accommodate special purposes, the handle 11 may also be curved or bent as required. A lengthwise extending internally threaded bore 15 is formed in the distal end 13 of the handle 11 to receive a correspondingly externally threaded end 21 of an extension section 18. The handle 11 has an indented or recessed area 17 on the dorsal aspect of the handle 11 near the distal end 13 thereof contoured to approximately fit a human thumb facilitating a user to maintain stability and control of the instrument during a surgical procedure. The handle 11 may be constructed of tubular or solid rod stock such as aluminum, stainless steel or other suitable material and may be provided in several different sizes as desired.

Figure 3:
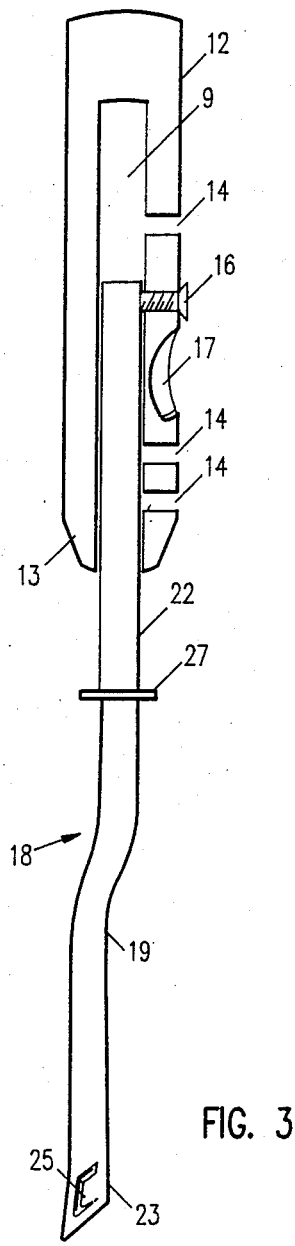
FIG. 3 is a cross-sectional view illustrating a second embodiment of a removable handle and interchangeable extension section constructed according to the principles of the present invention.
Figure 4:
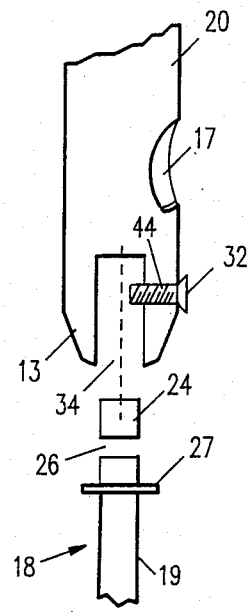
FIG. 4 is a cross-sectional view illustrating a third embodiment of a removable handle and interchangeable extension section constructed according to the principles of the present invention.

Referring now also to FIGS. 3 and 4, second and third preferred embodiments of the removable handle 12 and 20, respectively, and extension section 18 are shown. The handle 12 is generally round and preferably straight and is slightly bevelled at the distal end 13 thereof. A bore 9 is formed in the distal end 13 and extends lengthwise through a major portion of the handle 12. The bore 9 is smooth-walled and generally round to receive a generally round, elongated extension end 22 of extension section 18. A number of internally threaded holes 14 disposed in spaced relationship extending through the wall into the bore 9 are formed in the handle 12. The extension end 22 of extension section 18 may be inserted into the bore 9 to any desired depth and securely clamped in place by a set screw 16 tightened in the appropriate threaded hole 14 allowing any desired length of extension section 18 to protrude from the handle 12. The handle 20 (shown in FIG. 4) is similar in construction to the handle 11 described hereinabove. The bore 34 is smooth-walled rather than internally threaded and the extension end 24 is smooth-walled and slideably inserted into bore 34 with the flange 27 seated against the distal end 13 of the handle 20. An internally threaded hole 44 extending through the wall into the bore 34 is formed in the handle 20 near its distal end 13. Similarly a corresponding hole 26 is drilled transversely through the extension end 24 such that when the extension end 24 is inserted into and seated in the bore 34, a screw 32 tightened in the threaded hole 44 extends into the extension end hole 26 thereby securely and removably attaching the extension section 18 to the handle 20.

Figure 5:
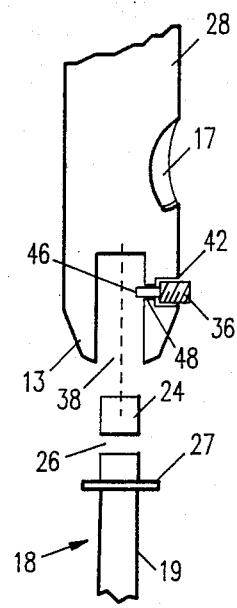
FIG. 5 is a cross-sectional view illustrating a fourth embodiment of a removable handle constructed according to the principles of the present invention.

Referring now also to FIG. 5, a fourth preferred embodiment of the handle 28 and interchangeable extension 18 is shown. The handle 28 is of similar construction as handle 29 (shown in FIG. 4) described hereinabove having a smooth-walled bore 38 extending lengthwise into the distal end 13 thereof. A relative large bore 42 is formed in the wall of handle 28 near its distal end 13 having a relatively small hole 46 extending from the bore 42 into bore 38. Similarly as described hereinabove, the extension end 24 has a corresponding hole 26 formed transversely therethrough. A push button mechanism 36 constructed in a well-known manner is mounted in the large bore 42 and has a spring-loaded pin 48 which extends through the small hole 46 into the bore 38. The tip of the pin 48 may be bevelled or otherwise adapted such that when the extension end 24 is inserted and seated in bore 38, the spring-loaded pin 48 snaps into the extension end hole 26 thereby securely and removably attaching the extension section 18 to the handle 28. Pushing inwardly on the push button mechanism 36 causes the pin 48 to be withdrawn from the extension end hole 26 allowing the extension section 18 to be removed from the handle 28.

Figure 6:
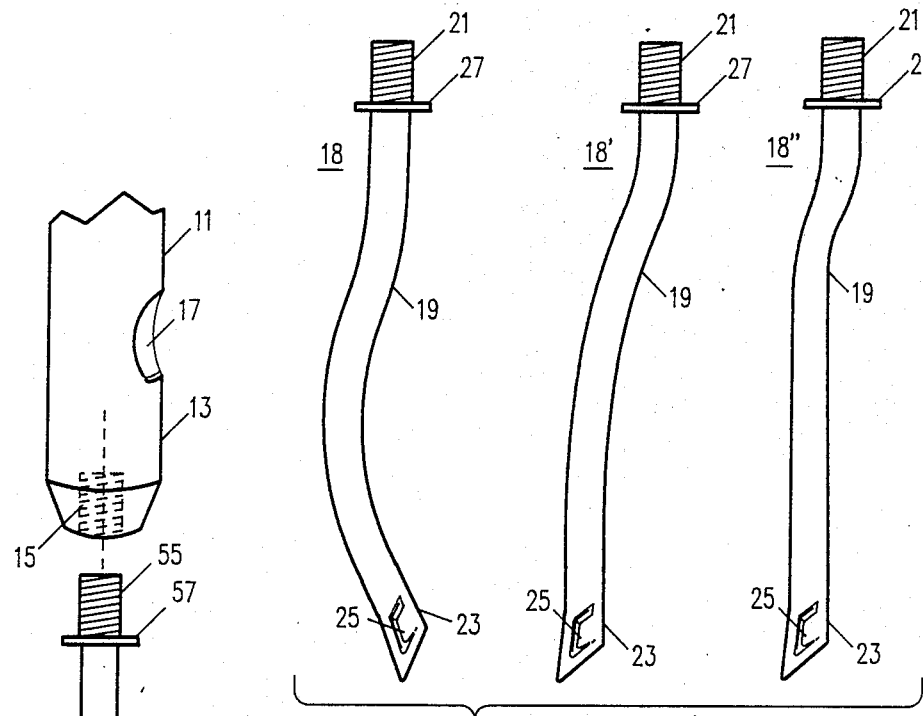
FIG. 6 is a perspective view illustrating various different sizes and curvatures of the interchangeable extension section shown in FIG. 2.
Figure 12:
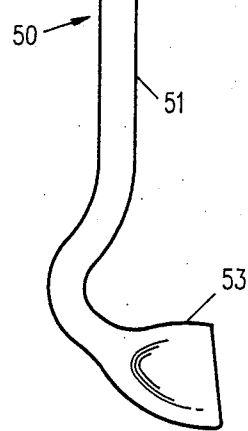
FIG. 12 is a perspective view of an interchangeable bladed extension section constructed in accordance with the principles of the present invention shown with the handle of FIG. 1.
Figure 13:
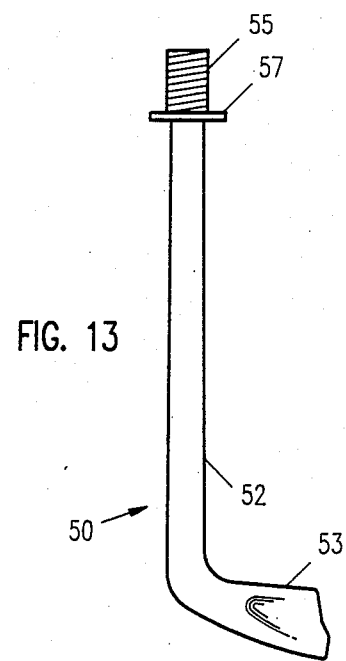
FIG. 13 is a perspective view of a different sized and shaped configuration of the bladed extension shown in FIG. 12.

Referring now also to FIG. 6, the interchangeable extension section 18 comprises a generally round shaft portion 19 having the distal end 23 thereof sufficiently flattened to facilitate forming a snap-on mounting tab 25 therein. The proximal end 21 or extension end 21 of the extension section 18 is externally threaded for easy insertion into the handle bore 15 and removable attachment to the handle 11. The proximal end 21 may also be formed as an elongated, generally round and smooth-walled shaft 22 or may be smooth-walled having a transverse hole formed therethrough (as shown in FIGS. 3, 4 and 5). A flange 27 separates the threaded end 21 from the extension shaft portion 19 ensuring that the extension section 18 is inserted in the handle bore 15 to the proper depth and that the handle bore 15 threads are not damaged. The snap-on mounting tab 25 is formed in any well-known manner and facilitates the installation of various different sized and shaped blade sections 30 (as shown in FIGS. 11a–11f). The extension section 18 may be fabricated from tubular or solid stock of any suitable material such as stainless steel and may be provided in various different sized and shaped configurations 18, 18' and 18" (as shown in FIGS. 2, 3, 4, 5 and 6) to adapt to the various curvatures of the bones encountered in the human body.

Figure 8:
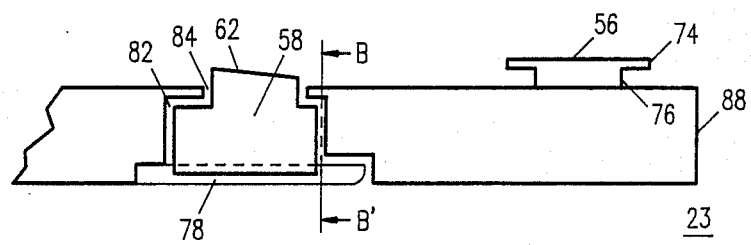
FIG. 8 is a cross-sectional side view taken along section A-A' of the spring-loaded quick release mechanism shown in FIG. 7.
Figure 9:
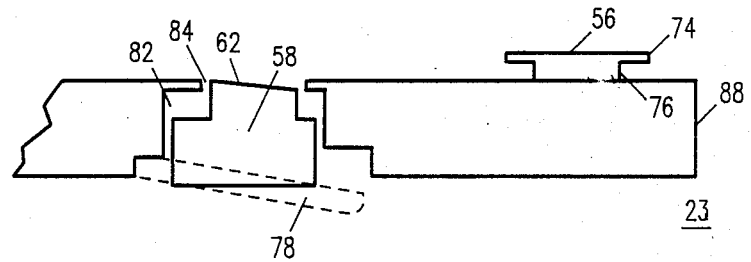
FIG. 9 is a cross-sectional side view of the spring-loaded quick release mechanism shown in FIG. 8 illustrating the action of the push-button release.
Figure 10:
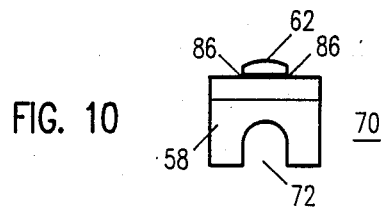
FIG. 10 is a cross-sectional front view taken along B-B' of the push-button shown in FIGS. 8 and 9.
Figure 11E:
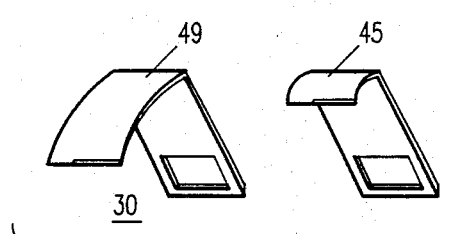
FIGS. 11a–11f are perspective views illustrating various different sized and shaped removable blade sections constructed according to the principles of the present invention.
Figure 11F:
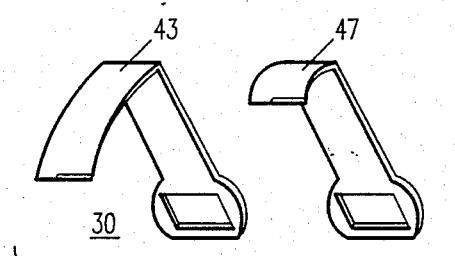
Figure 11C:
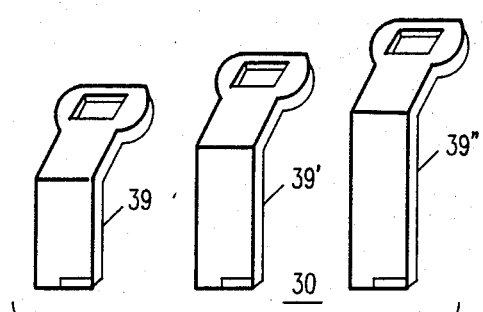
Figure 11D:
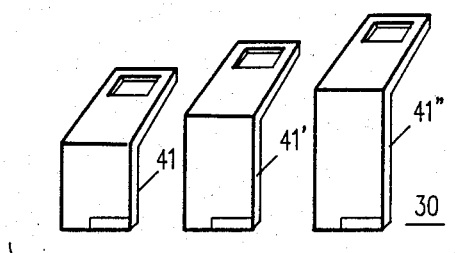
Figure 11A:
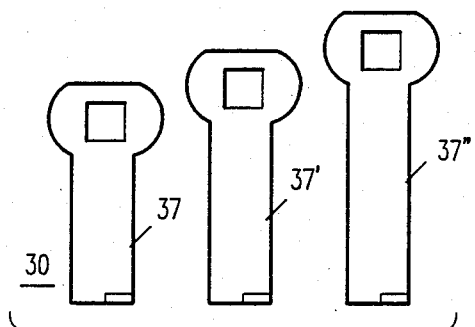
Figure 11B:
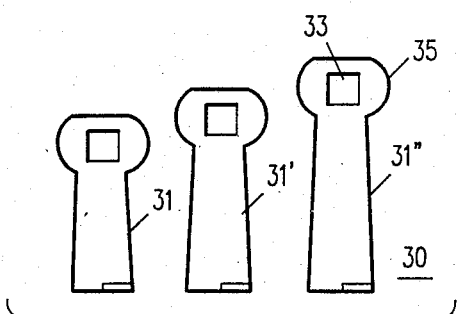

Referring now also to FIGS. 8, 9 and 10, a push button snap-on mounting mechanism is shown. A push button 70 comprising a solid block 58 with a smaller dimensioned button 62 protruding from the top surface of the block 58 and having a channel 72 formed in the bottom surface of the block 58 is mounted on a metal rod 78 in a shaped cavity 82 formed in the distal end 23 of an extension section 19. The metal rod 78 is fixedly attached to the bottom side of the extension section end 23 to form a cantilever spring disposed in the channel 72 such that the block 58 straddles the metal rod 72 and is retained in the cavity 82. A hole 84 extending from the cavity 82 through the top side of the extension section end 23 allows the button 62 to protrude from the top surface of the extension section end 23. Shoulders 86 formed by the block 58 and button 62 retain the push button 70 in the cavity 82. A short mounting post 76 is fixedly attached to the top surface of the extension section end 23 between the push button 70 and the end 88 of the extension section in spaced relationship with the protruding button 62. The mounting post 76 has a flattened top 56 having a larger diameter than the mounting post 76 forming flange 74.

Figure 7:
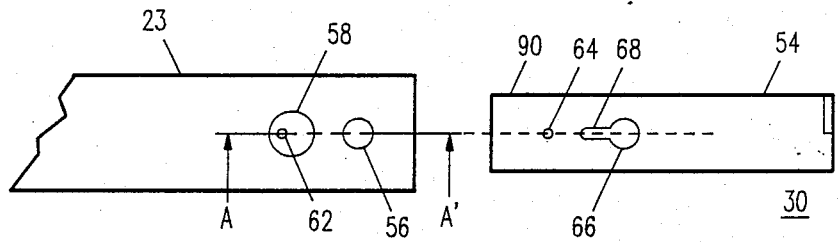
FIG. 7 is a top view of an extension section and a blade section illustrating a spring-loaded, quick release mechanism for removable attaching a blade section to an extension section.

Referring now also to FIG. 7, snap-on blade section 30 comprises a blade portion 54 and a mounting end 90 having a keyhole slot 66, 68 and a button slot 64 formed therein. The larger portion 66 of the keyhole slot is slightly larger than the mounting post flattened top 56 while the elongated slot 68 is of a slightly larger diameter than the mounting post 76. The button slot 64 is of a slightly larger dimension than the button 62.

To mount the blade section 30 on the extension section end 23, the blade mounting end 90 is placed over the top of the extension section end 23 and the large portion 66 of the keyhole slot aligned with the mounting post top 56. The blade section 30 is slipped over the mounting post 76 with the flattened top 56 protruding through the keyhole slot while the blade section 30 is pulled lengthwise away from the extension section end 23 sliding the mounting post 76 into the narrow slot portion 68 of the keyhole slot. The flange 74 engages the surface of the blade section 30 at the edges of the keyhole slot thereby holding the blade section 30 firmly against the top surface of the extension section end 23. As the blade section 30 slips over the mounting post 76, the push button 70 is depressed (as shown in FIG. 9) as the blade section end 90 slides over it. When the mounting post 76 is properly lined up in the elongated portion 68 of the keyhole slot, the push button 70 is pushed upwardly by the cantilever spring 78 and the button 62 snaps into the button slot 64 thereby retaining the blade section 30 securely in place. To remove the blade section 30 from the extension section end 23, the push button 70 is depressed freeing the blade section 30 to be slipped off the mounting post 76.

Referring now also to FIGS. 11a–11f, the interchangeable, snap-on blade section 30 comprises a blade portion 31 and a mounting or proximal end 35. An alternative mounting mechanism for the blade section 30 comprises a mounting slot 33 formed in the proximal end 35 thereof. The mounting slot 33 engages the mounting tab 25 (shown in FIG. 6) in a well-known manner to provide snap-on removable attachment of the blade section 30 to the extension section 18. The blades 30 may be fabricated from flat stock and are provided in various different sized and shaped blade configurations: straight-flared 31, 31' and 31", straight 37, 37' and 37" partially angulated 45 degree 39, 39', 39", 41, 41' and 41" semi-curved 43, 45 and 180 degree curved 47, 49. The blades 30 further may be provided in two edge configurations; a three-quarter edged blade or a smooth, rounded one-quarter edged blade. The smooth, rounded one-quarter edged blade is designed to prevent severing a tendon inadvertently when performing surgical procedures in small, confined or visually restricted areas; for example, when removing the fibular sesamoid bone, the smooth edge of the blade 30 is plantar thus preventing the severance of the flexor hallecis longus tendon during a fibular sesamoidectomy procedure.

Figure 14A:
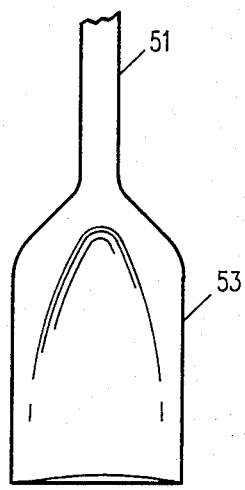
FIGS. 14a, 14b and 14c are perspective views illustrating the configuration of the blade portion of the bladed extensions shown in FIGS. 12 and 13.
Figure 14B:
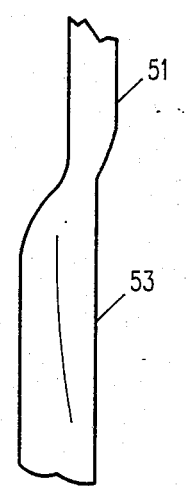
Figure 14C:
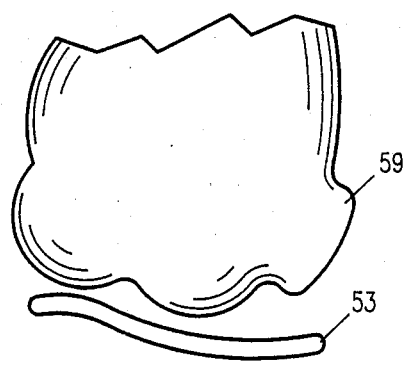

Referring now to FIGS. 1, 12, 13, and 14a–14c, a capsular releasing instrument comprises the handle 11 removable attached to a number of interchangeable different sized and curved bladed extension sections 50. The removable handle 11 is constructed as described hereinabove and may be provided in a number of sizes as desired. A bladed extension section 50 comprises a curved or straight shaft section or shaft 51 or 52, respectively, having a contoured blade 53 formed at the distal end thereof integrally therewith. The proximal end 55 of the bladed extension section 50 is externally threaded for easy insertion into the handle bore 15 and removable attachment to the handle 11. A flange 57 separates the threaded end 55 from the shaft 51 ensuring that the bladed extension section 50 is inserted in the handle bore 15 to the proper depth and the handle bore 15 threads are not damaged. The bladed extension section 50 may be provided in various different sized and curved or straight configurations as required to adapt to the various curvatures of the bones encountered in the human body. The bladed extension section 50 may also be fabricated as shown in FIGS. 3, 4 and 5 and similarly, may be used with the handles 12, 20 and 28 constructed as shown in FIGS. 3, 4 and 5 and described hereinabove. As illustrated in FIGS. 14a, 14b and 14c, the integral blade 53 is slightly flattened and contoured to accommodate the various curvatures of the bones ends 59 forming a joint. The bladed extension sections 50 may be fabricated from tubular or solid stock from stainless steel or other suitable material and are interchangeably attachable to one or more standard sized handles 11.

Figure 15:
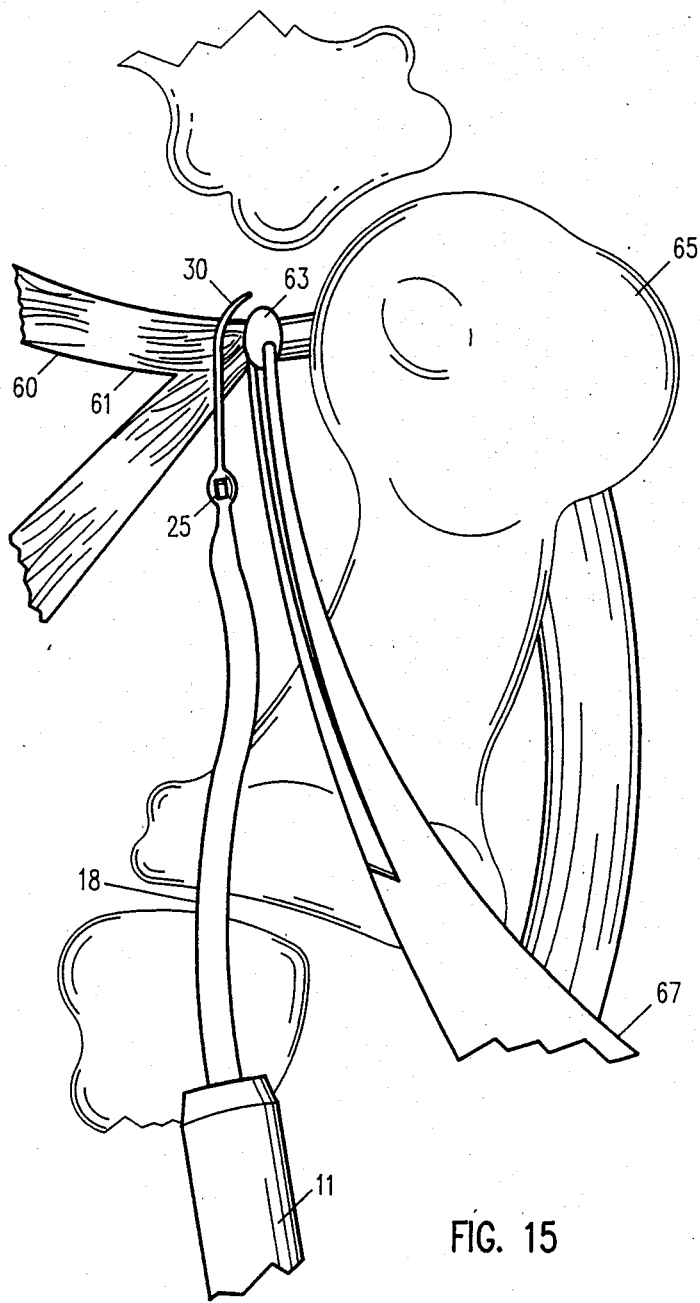
FIG. 15 is a perspective view illustrating the use of a surgical osteotome constructed according to the principles of the present invention.

Referring now to FIG. 15, the use of a surgical osteotome constructed according to the principles of the present invention is illustrated. A surgical osteotome instrument comprising a handle 11, an extension section 18 and a blade section 30 is utilized in the removal of a fibular sesamoid 63 from a bone 65 and the concomitant severance of the conjoint tendon 61 and related sesamoidal attachments. The fibular sesamoid 63 is removed with the aid of a sesamoid extractor instrument 67.

Figure 16A:
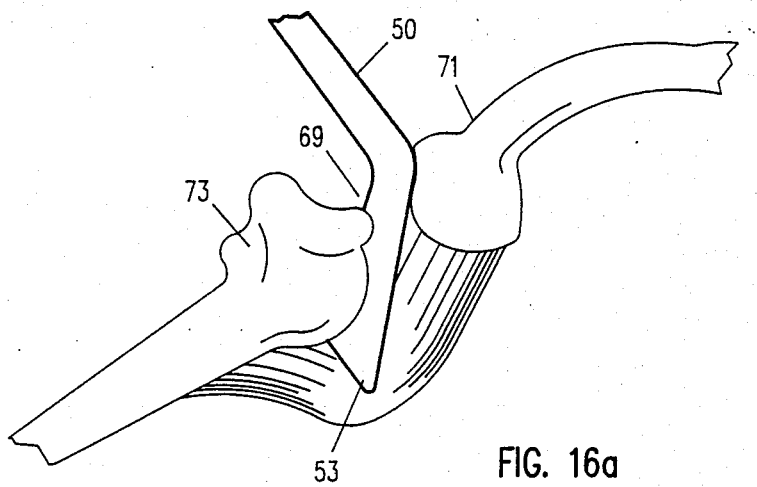
FIGS. 16a and 16b are perspective views illustrating the use of capsular releasing instruments constructed according to the principles of the present invention.
Figure 16B:
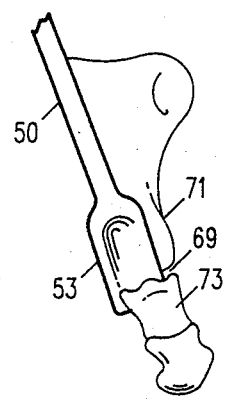

Referring now to FIGS. 16a and 16b, the use of a capsular releasing instrument constructed according to the principles of the present invention is illustrated. The blade 53 of the bladed extension section 50 is gently forced into the joint 69 formed between two bone ends 71 and 73 and the bone ends 71, 73 are forced apart thus opening the joint 69.

The surgical osteotome and capsular releasing instruments described herein may be fabricated from stainless steel or other suitable materials having sufficient flexibility and corrosion resistance.

Although the present invention has been described in its preferred form with a certain degree of particularity, it is understood that the present disclosure of the preferred embodiment has been by way of example and that numerous changes in the details of construction and the combination and arrangement of elements may be resorted to without departing from the spirit and scope of the invention as hereinafter claimed.

I claim:

1. A surgical instrument comprising:

an elongated, generally round handle having a lengthwise extending bore formed in a distal end thereof, said elongated handle having an indented area near said distal end contoured to accommodate a human thumb;

an elongated extension member, said extension member having a proximal end adapted for insertion in said bore for removably attaching said extension member to said elongated handle, said elongated extension member having a mounting surface formed adjacent a distal end thereof, a spring loaded push button mounted adjacent said extension member distal end biased for protruding through said mounting surface, said enlarged circular portion formed at the end of said slot away from said proximal end of said blade section, a mounting post protruding from said mounting surface adjacent said extension member distal end disposed in spaced relationship with said spring loaded push button, said mounting post disposed between said spring loaded push button and said extension member distal end, said mounting post having a flattened top forming a radially extending flange, said flange having a larger diameter than said mounting post; and a blade section having first and second apertures formed therethrough disposed in spaced relationship at a proximal end thereof, said first aperture forming a lengthwise extending elongated slot one end of which being an enlarged circular portion having a diameter slightly larger than said mounting post flattened top for receiving said flattened top, said enlarged circular portion formed at the end of said slot away from said proximal end of said blade section, the width of said elongated slot being slightly greater than the diameter of said mounting post, said second aperture adapted for engaging said spring loaded push button and preventing lengthwise movement of said blade section when said proximal end thereof is placed in overlaying relationship with the distal end of said elongated extension member, a lower side of said blade section in contact with said mounting surface, said flattened top protruding through said enlarged circular portion of said elongated slot, and said elongated slot displaced lengthwise for slidingly engaging said mounting post, said radially extending flange engaging said proximal end of said blade section retaining said proximal end of said blade section tightly against said mounting surface of said elongated extension member.

2. The surgical instrument as in claim 1 wherein said lengthwise extending bore is internally threaded and said proximal end of said elongated extension member is externally threaded and adapted to cooperate with said internally threaded bore for removably attaching said extension to said handle.

3. The surgical instrument as in claim 2 wherein said elongated extension member is interchangeable with each one of a plurality of elongated extension members, each one of said plurality of elongated extension members having a different size or configuration, each of said plurality of elongated extension members removably attachable to said handle.

4. The surgical instrument as in claim 3 wherein a plurality of said blade sections may be interchangeably and removably mounted at said distal end of each one of said plurality of elongated members, each one of said plurality of blade sections being of a different size or configuration.

5. The surgical instrument as in claim 4 wherein at least one of said plurality of blade sections comprises a semi-curved configuration.

6. The surgical instrument as in claim 4 wherein at least one of said plurality of blade sections comprises a 180 degree curved configuration.

7. The surgical instrument as in claim 4 wherein at least one of said plurality of blade sections comprises a partially angulated 45 degree configuration.

8. The surgical instrument as in claim 4 wherein at least one of said plurality of blade sections comprises a straight configuration.

9. The surgical instrument as in claim 4 wherein at least one of said plurality of blade sections comprises a flared-straight configuration.

10. The surgical instrument as in claim 1 wherein said handle includes mounting means, said mounting means adapted for removably attaching said extension member to said handle, said proximal end being selectively insertable in said bore to any desired depth.

11. The surgical instrument as in claim 10 wherein said mounting means comprises at least one internally threaded hole formed in a side wall of said bore and extending through said sidewall and at least one set screw for securely retaining said proximal end in said bore when said set screw is tightened in said threaded hole.

12. The surgical instrument as in claim 10 wherein said mounting means comprises a push button mechanism mounted in a sidewall of said handle, said push button mechanism including a spring-loaded pin protruding into said bore, said extension member proximal end adapted to engage said pin when said extension member proximal end is inserted into said bore, said push button mechanism for removably attaching said extension member to said handle.

13. The surgical instrument as in claim 1 wherein said surgical instrument is constructed of stainless steel.

14. The surgical instrument as in claim 1 wherein said handle is constructed of aluminum.

* * * * *